(12) United States Patent
Kim et al.

(10) Patent No.: US 9,139,852 B2
(45) Date of Patent: Sep. 22, 2015

(54) METHOD AND APPARATUS FOR PRETREATING BIOMASS USING INTERNAL HEAT

(75) Inventors: Jin Woo Kim, Seoul (KR); Jae Chan Park, Yongin-si (KR); Sung Min Park, Yongin-si (KR); Young Kyoung Park, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 742 days.

(21) Appl. No.: 12/967,578

(22) Filed: Dec. 14, 2010

(65) Prior Publication Data

US 2011/0143412 A1    Jun. 16, 2011

(30) Foreign Application Priority Data

Dec. 15, 2009    (KR) .......................... 10-2009-0124803

(51) Int. Cl.
| | |
|---|---|
| B01J 8/10 | (2006.01) |
| D21C 1/00 | (2006.01) |
| C12P 7/08 | (2006.01) |
| C12M 1/33 | (2006.01) |
| D21C 1/02 | (2006.01) |
| D21C 1/10 | (2006.01) |
| C12M 1/00 | (2006.01) |
| C12M 1/34 | (2006.01) |
| D21C 1/04 | (2006.01) |
| D21C 1/06 | (2006.01) |
| D21C 3/20 | (2006.01) |

(52) U.S. Cl.
CPC ........ *C12P 7/08* (2013.01); *C12M 41/12* (2013.01); *C12M 45/02* (2013.01); *C12M 45/06* (2013.01); *D21C 1/00* (2013.01); *D21C 1/02* (2013.01); *D21C 1/04* (2013.01); *D21C 1/06* (2013.01); *D21C 1/10* (2013.01); *D21C 3/20* (2013.01); *B01J 8/10* (2013.01); *Y02E 50/16* (2013.01); *Y02E 50/17* (2013.01)

(58) Field of Classification Search
CPC ...................................................... D21C 3/024
See application file for complete search history.

(56) References Cited

U.S. PATENT DOCUMENTS

| | | | | |
|---|---|---|---|---|
| 4,136,207 A | * | 1/1979 | Bender | ........................ 426/510 |
| 4,600,590 A |   | 7/1986 | Dale |   |
| 5,181,989 A | * | 1/1993 | White et al. | .................. 162/241 |
| 5,211,811 A |   | 5/1993 | Griggs et al. |   |
| 5,409,570 A |   | 4/1995 | Griggs et al. |   |
| 5,411,714 A | * | 5/1995 | Wu et al. | ........................ 422/232 |
| 5,451,296 A |   | 9/1995 | Pikulin et al. |   |
| 5,472,572 A |   | 12/1995 | White et al. |   |
| 5,520,783 A |   | 5/1996 | White et al. |   |

(Continued)

FOREIGN PATENT DOCUMENTS

| | | | | |
|---|---|---|---|---|
| CH | 604805 A | * | 9/1978 | |
| GB | 1381728 A | * | 12/1976 | |

OTHER PUBLICATIONS

English language machine translation of CH 604 805 (Sep. 1978).*

*Primary Examiner* — Jennifer A Leung
(74) *Attorney, Agent, or Firm* — Leydig, Voit & Mayer, Ltd.

(57) ABSTRACT

A method for pretreating a biomass, in which a water-reactive anhydride contacts a biomass, is disclosed. The biomass is pretreated using internal heating by an exothermic reaction. Further, an apparatus for pretreating a biomass having a reaction part including an inlet part and an outlet part for the water-reactive anhydride is disclosed.

12 Claims, 4 Drawing Sheets

(56) References Cited

U.S. PATENT DOCUMENTS

| | | |
|---|---|---|
| 5,863,389 A | 1/1999 | White et al. |
| 6,416,621 B1 * | 7/2002 | Karstens ................. 162/22 |
| 6,419,788 B1 * | 7/2002 | Wingerson ................. 162/14 |
| 2008/0008783 A1 | 1/2008 | Dale |
| 2008/0293114 A1 | 11/2008 | Foody et al. |
| 2009/0011474 A1 | 1/2009 | Balan et al. |
| 2009/0056889 A1 * | 3/2009 | Ren et al. ................. 162/38 |
| 2009/0221814 A1 * | 9/2009 | Pschorn et al. ................. 536/128 |

* cited by examiner

METHOD AND APPARATUS FOR PRETREATING BIOMASS USING INTERNAL HEAT

CROSS-REFERENCE TO RELATED APPLICATION

This application claims the benefit of Korean Patent Application No. 10-2009-0124803, filed on Dec. 15, 2009, and all the benefits accruing therefrom under 35 U.S.C. §119, which is hereby incorporated by reference as if fully set forth herein.

BACKGROUND

1. Field

The disclosure relates to a method of pretreating a biomass using internal heating, a method of producing biofuels or biochemicals using the same, and an apparatus for pretreating the biomass.

2. Description of the Related Art

With globally increasing concern about exhaustion of resources and pollution of the environment by overuse of fossil fuels, new and renewable substitute energy resources for stably and continuously producing energy are being considered. In the ongoing development of such substitute energy resources, techniques for producing ethanol and other biofuels from biomass have been receiving considerable attention. Various fuels such as alcohol, diesel, and hydrogen; or chemicals such as antigens, antibodies, hormones, amino acids, haptenes, proteins and enzymes can be produced from biomass. To produce biofuel or a biochemical, such as ethanol, using biomass, pretreatment and enzymatic hydrolysis of the biomass is performed to convert lignocellulosic polysaccharide components into fermentable sugars for fermentation.

For example, a lignocellulosic biomass can be pretreated by a physical method such as milling and steam explosion or by a chemical method such as acid or base hydrolysis. Such pretreatments are performed at high temperature and use a large amount of energy, chemicals, and industrial water, resulting in high production costs.

SUMMARY

A method for pretreating a biomass is provided. The method for pretreating a biomass includes contacting a water-reactive anhydride with a water-containing biomass in a closed reactor to induce internal heating, wherein the temperature in the closed reactor is adjusted by at least one among the following: a) the input amount or the input flow rate of the water-containing biomass; b) the ratio of the dry weight of the biomass to the weight of water; c) the pressure of the water-reactive anhydride; d) the input amount or the input flow rate of the water-reactive anhydride.

A method of producing a biofuel or a biochemical using the above-mentioned pretreatment method is also provided. The method of producing a biofuel or a biochemical includes converting a polysaccharide obtained from the pretreated biomass by the method disclosed herein into monosaccharides, and fermenting the monosaccharides to produce a biofuel or a biochemical.

Further, an apparatus for pretreating a biomass, which can be used with to the above-mentioned pretreatment method, is provided.

The apparatus for pretreating a biomass includes a reaction part for pretreating a biomass including an inlet part which is formed at one end and through which a water-reactive anhydride can be input, and an outlet part which is formed at the opposite end and through which the water-reactive anhydride can be output; a biomass supply part for supplying a biomass to a reaction part; and a separation part for separating components extracted from the biomass in the reaction part.

BRIEF DESCRIPTION OF THE DRAWINGS

Exemplary embodiments are described in further detail below with reference to the accompanying drawings. It should be understood that various aspects of the drawings may have been exaggerated for clarity.

DETAILED DESCRIPTION

Figure 1:
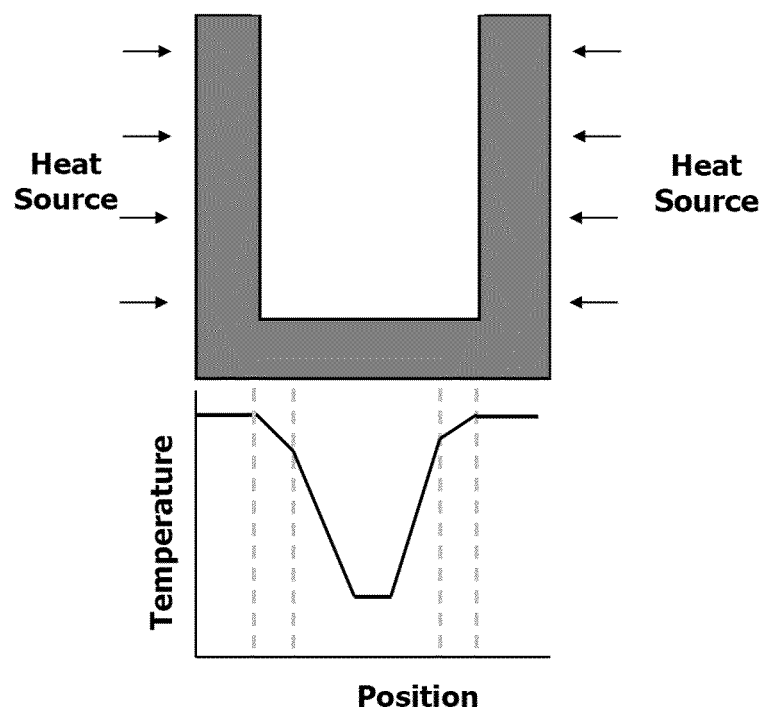
FIG. 1 schematically shows a reactor with an externally supplied heat source (upper panel) and a graph (lower panel) representing temperature as a function of position across the reactor when heat is supplied by the external heat source.

Various exemplary embodiments will now be described more fully with reference to the accompanying drawings in which some exemplary embodiments are shown. In the drawings, the thicknesses of layers and regions may be exaggerated for clarity.

The terms used herein are defined as follows:

The term "biomass" refers to substances containing an organic component, which can be used in a production system producing energy such as ethanol, carbohydrates, gasoline, natural gas, methane, biodiesel and hydrogen gas, electricity, plastics, polymers, nutrients (for a human or an animal), proteins, biomolecules, drugs (for a human or an animal), fertilizers or other products, or a combination thereof.

The term "lignocellulosic biomass" refers to plant biomass composed of cellulose, hemicellulose, and lignin which can be used for energy on the basis of environmentally friendly standards. For example, lignocellulosic biomass may include agricultural wastes and residues such as corn stover, wheat straw, rice straw, and sugar cane bagasse. Lignocellulosic biomass may also include wood, wood energy crops, wood wastes and residues (for example, thinned coniferous trees, tree bark waste, sawdust, paper/pulp industrial waste vapor, and wood fiber), grasses such as switchgrass, garden wastes (e.g., cut grass, fallen leaves, cut wood, and bush), and vegetable wastes.

The term "pretreatment of a biomass" refers to a process of changing the chemical or physical structure of the biomass to permit easier degradation into monosaccharides. This pretreatment permits separation of components of the biomass such that enzymatic saccharification can be performed at higher rates with better yields. For example, pretreatment of biomass may involve changing chemical bonding, conformation, or the three-dimensional structure of the components, thereby removing non-saccharide components, and in order to facilitate subsequent enzymatic saccharification. Pretreatment of biomass may also involve a change in molecular structure, oxidation of components in the biomass, changes in average molecular weight, average degree of crystallization, surface area, degree of polymerization, degree of porosity, and degree of branching, grafting, and changes in size of a crystallized region and in size of the entire mass.

The term "biofuel" refers to fuel produced partially or entirely from a biomass.

The term "biochemical" herein refers to a chemical produced partially or entirely from a biomass. The biochemical includes cell-constituting materials, genetic materials, carbon compounds, and organic materials which influence metabolism, synthesis, transportation or signal transduction of organism (including metal organic compounds).

The term "water-reactive anhydride" refers to an anhydride having an exothermic reaction with water. The term "internal heating" refers to a reaction generating heat by an exothermic reaction in a closed reactor.

The terms "lignin extract", "hemicellulose extract", and "cellulose extract" refer to extracts having lignin, hemicellulose, and cellulose as the main component, respectively, and also having other components. For example, during the extraction of lignin, hemicellulose and cellulose can be extracted at the same time, but the content of the lignin extracted is relatively higher than those of the other components. Thus, each extract does not contain only lignin, hemicellulose, or cellulose, but also contains other components, which are mixed with one another.

Unless described otherwise, all technical and scientific terms used herein have the same meanings as those generally understood by one of ordinary skill in the art.

1. Method for Pretreating Biomass

A method for pretreating a biomass according to an exemplary embodiment includes contacting a water-reactive anhydride with a water-containing biomass in a closed reactor to induce internal heating, wherein the temperature in the closed reactor is adjusted by at least one among the following: a) the input amount or the input flow rate of the water-containing biomass; b) the ratio of the dry weight of the biomass to the weight of water; c) the pressure of the water-reactive anhydride; d) the input amount or the input flow rate of the water-reactive anhydride.

The pretreating method as disclosed herein may allow the temperature of the reactor to be increased by internal heating to a reaction temperature sufficient for the pretreating, without heat supplied from outside the reactor. By using the anhydride, the internal heating is carried out in a short time and the temperature distribution in the closed reactor becomes uniform. Therefore, the pretreatment time and production of by-products inhibiting subsequent reactions are minimized in the disclosed pretreatment method. Further, sufficient internal heating is induced with a small amount of water; thus, a large amount of industrial water is not needed.

Figure 2:
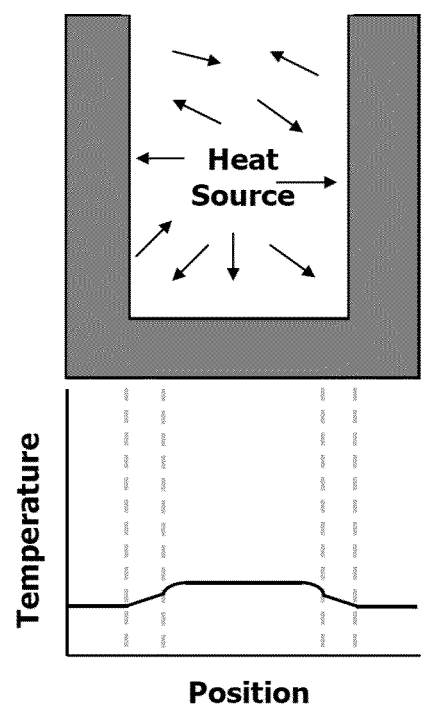
FIG. 2 schematically shows a reactor in which heat is generated within the reactor by an internal heating reaction (upper panel) and a graph (lower panel) representing temperature as a function of position across the reactor during the internal heating reaction.

Hereafter, the difference between when a biomass is pretreated using internal heating according to an exemplary embodiment of the present invention, and when a biomass is pretreated using an external heating source according to a conventional pretreatment method is seen. FIGS. 1 and 2 schematically show temperature distribution within a reactor as a function of position across the reactor, when heat is supplied by a heat source external to the reactor according to a conventional pretreatment method (FIG. 1) and when an internal heating reaction is induced within the reactor according to an exemplary embodiment of the present invention (FIG. 2).

FIG. 1 schematically shows that the temperature is higher at positions within the reactor that are closer to the heat source, than at positions that are farthest from the heat source. When heat is applied to the reactor walls from an external source, in order to obtain a desired temperature in the middle of the reactor, a temperature higher than the desired temperature will be achieved at the points in the reactor closer to the external heat source. Such high temperatures result in excessive reaction of monosaccharides produced, resulting in their conversion into furfural, hydroxymethylfurfural (HMF), and the like, which inhibit subsequent saccharification or fermentation processes.

In contrast, FIG. 2 schematically shows the temperature distribution resulting from the disclosed pretreatment method in which an internal heating reaction occurs. FIG. 2 shows that when an internal heating reaction occurs within the reactor, thus providing a randomly distributed heat source within the reactor, the temperature distribution within the reactor is generally more uniform. Such a rapidly produced and uniform temperature distribution throughout the reactor minimizes the time needed for the pretreatment reaction and production of byproducts inhibiting subsequent reactions.

The internal heating is generated in the closed reactor by an exothermic reaction of a water-reactive anhydride with a water containing biomass. According to the example shown in Reaction Formula (1), anhydrous ammonia is a gas that dissolves in water to produce aqueous ammonia (ammonium hydroxide). The process is an exothermic reaction generating heat that can be used to internally heat a closed reactor.

$$NH_3(g) + H_2O(l) \rightarrow NH_4^+ + OH^- + Q \quad (1)$$

In the above reaction equation, Q represents the amount of heat produced in the dissolution reaction.

When gaseous ammonia contacts a water containing biomass under pressure in a closed reactor, it easily penetrates into the biomass due to its high mobility, resulting in a uniformly distributed exothermic reaction. In addition, since the exothermic reaction of the ammonia gas occurs in a short period of time, the pretreatment may be performed effectively in a short reaction time, for example, in about 0.1 to 3 hours, or more specifically, in about 0.5 to 1 hour.

In aqueous solution, ammonia deprotonates a small fraction of the water to give ammonium and hydroxide according to the following equilibrium shown in Reaction Formula (2).

$$NH_3 + H_2O \Leftrightarrow NH_4^+ + OH^- + Q \quad (2)$$

According to Reaction Formula (1), the amount of heat generated is proportional to the amount of the anhydride dissolved in water. Thus, methods for increasing temperature of the reactor using such an internal heating reaction are as follow.

The input amount or the input flow rate of the water-containing biomass can be increased. In other words, increase the amount of water contained in the biomass, or increase the input flow rate of the water-containing biomass when it is supplied continuously.

The ratio of the weight of the dry biomass to the weight of water (or Solid/Liquid ratio), an indicator of how wet the biomass is, can be decreased. As the Solid/Liquid ratio becomes smaller, i.e., the biomass becomes wetter, the temperature of the reactor becomes higher.

The pressure of the water-reactive anhydride in a reactor can be increased. As the pressure of the anhydride increases, the solubility of the anhydride increases, resulting in an increase in the amount of internal heat produced in the reactor.

The input amount or input flow rate of a water-reactive anhydride can be increased. When the input amount of the anhydride or the input flow rate of the anhydride in a continuous injection process increases, the anhydride's pressure in a closed reactor becomes higher. As noted above, as the pressure of the anhydride increases, its solubility increases, resulting in an increase in the amount of internal heat produced in the reactor.

Further, to maintain a constant temperature or to increase the temperature of the closed reactor without an external heat supply, the anhydride and water can be supplied to the reactor at the same speed or at a higher speed than the anhydride dissolves in water. Therefore, the water-reactive anhydride and/or water-containing biomass may be continuously injected into the reactor.

The amount of water contained in or supplied to the biomass is not particularly limited, but should be sufficient to support the exothermic reaction with the water-reactive anhydride. An appropriate amount of water to support internal heating for the pretreatment method depends on the type of water-reactive anhydride to be used and the equivalent ratio of water:anhydride in the exothermic reaction. Generally an appropriate amount of water contained in the biomass is about 0.5 to about 5 times, or about 0.5 to about 3 times the dry weight of the biomass. The amount of water used in the disclosed pretreatment is considerably smaller than the amount used in conventional pretreatment methods, in which the amount of water is about 10 to about 20 times the dry weight of the biomass. As a result, production costs for supply of industrial water, heating and cooling of the industrial water, and treatment of waste water can be reduced in the disclosed method. Additionally, throughput can be increased.

If the biomass is dry or contains insufficient water to support an internal heating reaction, external water can be supplied to the biomass to obtain an adequate level of water in the biomass. The water may be supplied continuously or discontinuously to the dry biomass by spraying or dipping, but is not limited thereto. However, when the biomass contains sufficient water to support an internal heating reaction, no additional supply of water is needed.

Also the amount of the water-reactive anhydride is not particularly limited, and may vary depending on its solubility in water. As the pressure of the ammonia gas rises, more ammonia dissolves (up to saturation) and the amount of internal heat increases. For a gas, the solubility of the gas in a liquid at a particular temperature can be indicated by the partial pressure of the gas above the liquid, according to Henry's law shown in Equation (3).

$$P=kc \quad (3)$$

In Equation (3), k is the Henry constant (a temperature-dependant constant), p is the partial pressure of the gas (atm), and c is the molar (mol/L) concentration of the gas dissolved in the liquid.

The solubility of a gas in a solvent generally increases as the temperature decreases, the pressure increases, or the attraction with the solvent increases. For a given solvent, gas solubility may be changed by varying temperature. For example, with respect to 100 ml of water, the solubility of ammonia is 89.9 g/100 ml at 0 r, 52.0 g/100 ml at 20° C., and 7.4 g/100 ml at 96° C. Thus, by consideration of the solubility of the water-reactive anhydride and the reaction temperature, the water-reactive anhydride may be added to the volume of water in the biomass at a concentration (and/or pressure) to form a saturated solution.

The temperature in the closed reactor, i.e., the reaction temperature, may be increased by the internal heating from ambient temperature to the desired temperature. The reaction temperature achieved by the internal heating may vary according to the kind of water-reactive anhydride, the pressure of the water-reactive anhydride, or the method of injecting the water-reactive anhydride (provided that water is contained sufficiently). For example, when anhydrous ammonia is continuously supplied to a reactor at 50 psi, the reaction temperature may be increased up to about 80° C., and when the anhydrous ammonia is continuously supplied to a reactor at 120 psi, the reaction temperature may be increased up to approximately 120° C. Additionally, when the process of pretreating a biomass is performed at an excessively high temperature, excessively-degraded products are produced that include inhibitory factors to subsequent process steps, e.g., saccharification, and thus the yield of monosaccharides can be reduced. For example, when pretreatment is performed at a temperature ranging from approximately 140 to 250° C., hemicellulose is excessively degraded into furfural, and cellulose is excessively degraded into hydroxyfurfural. Therefore, the reaction temperature at which the pretreatment of the biomass can be performed without excessive degradation to inhibitory by-products may range from approximately 60 to 130° C. To increase the reaction temperature of a reactor from ambient temperature to about 60~130° C. and maintain the reactor at that temperature, the pressure of the water-reactive anhydride with respect to the biomass may be approximately 10 to 500 psi, or 20 to 130 psi (provided that the amount of water in the biomass is sufficient).

Examples of the biomass may be, but are not particularly limited to, a lignocellulosic biomass, and an algae biomass (green, brown or red algae). A source of the lignocellulosic biomass may be, but is not limited to, rice straw, hard wood, soft wood, herbs, recycled paper, waste paper, core, pulp and paper wastes, waste wood, thinned wood, cornstalk, corn cobs, chaff, wheat straw, sugar canestalk, palm tree residual products, bagasse, agricultural residual products, agricultural wastes, excretions of livestock, or a mixture thereof.

The water-reactive anhydride is an acidic anhydride gas or a basic anhydride gas. The water-reactive anhydride may be, but is not particularly limited to, anhydrous ammonia, hydrogen sulphide ($H_2S$), hydrogen chloride (HCl), carbon dioxide ($CO_2$), or a mixture of at least two of the foregoing.

The water-reactive anhydride may be input to a reactor in a forward or a reverse direction relative to the direction in which the biomass is input to the reactor. When the gas is input in the reverse direction, mixing of the gas with the biomass may be more effective resulting in higher reaction efficiency.

In some cases, during the internal heating reaction, a material having an exothermic reaction with the water-reactive anhydride or water may be further added to the reactor. For example, an aldehyde or an alkylene oxide can be added to the reactor in addition to anhydrous ammonia to stimulate the exothermic reaction of the anhydrous ammonia dissolution, thereby increasing the internal heat of reaction produced.

In addition, the water-reactive anhydride may be a substance dissolving or hydrolyzing one or more of the biomass components in the solution state. For example, when a lignocellulosic biomass containing water is treated with anhydrous ammonia, aqueous ammonia is produced. The aqueous ammonia can dissolve lignin from the lignocellulosic biomass, so that the amount of the lignin extracted may be about 30%, 40%, 50%, 60%, or more of the initial amount of lignin in the biomass.

An exemplary embodiment of a pretreatment method of a lignocellulosic biomass will be described hereinafter, with reference to FIGS. 3 and 4.

Figure 3:
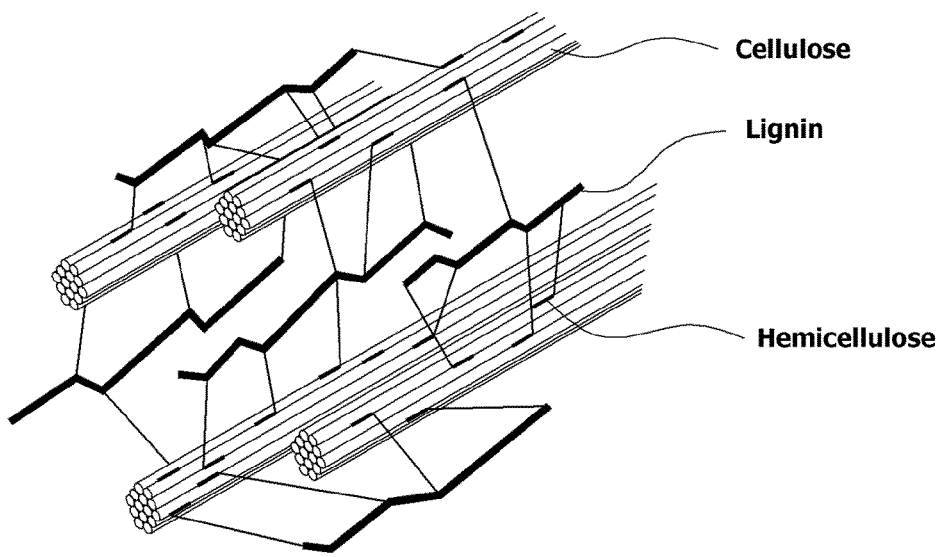
FIG. 3 is a schematic diagram of the structure of lignocellulose.

FIG. 3 shows a general schematic representation of lignocellulose, in which lignin is covalently bound to hemicellulose, which is hydrogen-bonded to cellulose. Generally, lignocellulose has a structure in which a central linear cellulose microfibril is surrounded by molecules of hemicellulose, and molecules of lignin surround the hemicellulose.

Figure 4:
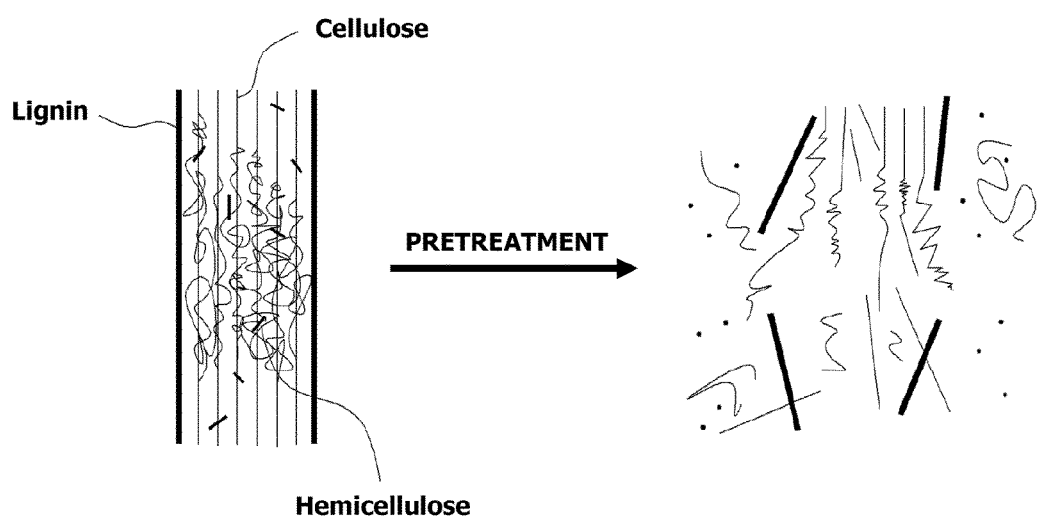
FIG. 4 schematically shows a lignocellulose pretreatment process producing structural modification of the lignocellulose.

FIG. 4 shows the pretreatment process of the lignocellulose which breaks the interconnections between lignin, cellulose, and hemicellulose. Because the conventional pretreatment process is carried out for a long time at high temperature under acidic condition, by-products of excessive degradation, such as furfural and HMF, are generated. Such by-products are inhibitory to subsequent saccharification and fermentation processes.

However, pretreatment using internal heating using ammonia gas is performed under basic conditions, and the biomass is pretreated within about 30 minutes to 1 hour at a temperature of about 130° C., thereby minimizing generation of by-products. Specifically, as lignin is extracted first of all, hemicellulose or cellulose may be subsequently extracted at a low temperature in a short time as compared to conventional pretreatment methods. As a result, the production of by-products of excessive polysaccharide degradation can be reduced. That is, when the pretreatment method disclosed herein is used, such excessive degradation of polysaccharides can be prevented.

Consequently, the recovery rate and availability of fermentable sugars produced from the biomass can be significantly increased. For example, cellulose extracted from biomass pretreated with the method disclosed herein will require a reduced amount of the enzyme to be used in the saccharification process to produce biofuels or biochemicals, resulting in decreased production costs, and also the reaction rate can be increased, resulting in an increase in saccharification yield.

After the lignin is extracted from the biomass, the aqueous ammonia can be dehydrated, and then compressed and recycled in other reactions. Methods of dehydration of aqueous ammonia to recover anhydrous ammonia are known in the art. During the compression process, cooling water is yielded, which may be also recycled.

Lignin is a hydrophobic polymer having a high molecular weight and a complicated structure, in which methoxylated p-coumaryl alcohol, coniferyl alcohol, and sinapyl alcohol are polymerized, thereby containing a large amount of aromatic compounds. Accordingly, degradation of the lignin results in production of phenolic compounds. The phenolic compounds produced are inhibitory to cell growth in saccharification and fermentation processes using enzymes or microorganisms. Therefore a washing process may be performed on the biomass. Through the washing process, lignin or residual bases may be removed. The lignin removed can be used in a variety of ways, e.g., as fuel for a steam or power plant boiler without specific treatment or as a phenol-based chemical substance after degradation.

The pretreatment method may further include adding a second solvent that dissolves a polysaccharide to degrade the polysaccharide into hexose and pentose molecules. Residual solid biomass components are left after treatment with the solvent. The method can further include extracting residual cellulose from the residual solid biomass components.

Hemicellulose and/or cellulose are extracted by adding a second solvent to the biomass. The second solvent may be a liquid or a gas which can dissolve at least a part of the hemicellulose and/or cellulose in the biomass, for example, about 50, 60, 70, 80%, or more.

For example, the second solvent may be an acid in liquid form, having a pH of 6.5 or less. The second solvent may be sulfurous acid ($H_2SO_3$), sulfuric acid ($H_2SO_4$), hydrogen chloride (HCl), phosphorous acid ($H_3PO_3$), nitric acid ($HNO_3$), acetic acid, peracetic acid (peroxyacetic acid), or a mixture thereof. The second solvent may have a concentration ranging from about 0.1 to about 10 wt %, about 0.5 to about 5 wt %, or about 0.5 to about 3 wt %.

Pentose and hexose concentration included in a liquid extract by adding the second solvent may be about 5 to about 10 wt % and about 1 to about 3 wt %, respectively.

The residual solid component of the biomass, residual cellulose, may then be extracted from the biomass in the reactor such that the initial amount of cellulose is reduced by about 70, 80, 85%, or more.

In one embodiment, the method for pretreating a biomass may include the following steps: optionally, supplying water to a biomass to produce a water-containing biomass; contacting a water-reactive anhydride with the water-containing biomass to induce internal heating, and to extract and remove lignin from the biomass; adding a solvent that dissolves hemicellulose and/or cellulose or that degrades hemicellulose and/or cellulose to pentose and hexose units; and extracting residual cellulose from residual solid biomass components.

Using such biomass pretreatment methods, excellent economical efficiency can be achieved by reducing water and energy consumption, and by minimizing or eliminating production of lignin and saccharide degradation by-products with inhibitory effects on downstream processes, such as saccharification and fermentation.

2. Method of Producing Biofuels or Biochemicals

In another aspect, a method of producing biofuels or biochemicals using a biomass pretreated by the above-described method is provided. The biofuels or biochemicals may be, but are not limited to, alcohols such as ethanol, n-propanol, isopropanol, n-butanol, alkane-based compounds, $C_3$-$C_6$ chemical compounds, organic acids, and a mixture thereof.

The method of producing a biofuel or biochemical according to an exemplary embodiment includes: converting a polysaccharide obtained from the pretreated biomass by the method for pretreating the biomass, into monosaccharides by saccharification; and fermenting the monosaccharides to produce the biofuel or biochemical.

In some cases, the method of producing a biofuel or biochemical may further include separating and/or purifying the biofuel or biochemical from the fermentation culture.

Saccharification is the process of converting a polysaccharide into monosaccharides. Saccharification of a polysaccharide may be performed using enzymes, acids, or microorganisms. For example, saccharification may be performed enzymatically by mixing one or a mixture of industrial hydrolases, such as α-amylase, glucoamylase, pectinase, xylanase, cellobiase, and cellulase, with the polysaccharide under conditions that support the hydrolytic reaction of the enzyme. Saccharification may also be performed by mixing the polysaccharide with dilute sulfuric acid or by adding the polysaccharide to aculture of a microorganism capable of producing hydrolytic enzymes, such as the above-mentioned enzymes. The microorganism may be a bacterium, a yeast, or a mold. A combination of microorganisms may also be used. The polysaccharide saccharified can be isolated from or in a mixture with the pretreated biomass.

Fermentation, as shown in Reaction Formulae (4) and (5), converts a hexose or pentose into ethanol using enzymatic pathways of fermenting microorganisms.

$$C_6H_{12}O_6 \rightarrow 2C_2H_5OH + 2CO_2 \qquad (4)$$

$$3C_5H_{10}O_5 \rightarrow 5C_2H_5OH + 5CO_2 \qquad (5)$$

Fermentation may be performed using a microorganism such as yeast. For example, a strain using $C_5$ sugars and a strain using $C_6$ sugars may be separately cultured under conditions to produce biofuels or biochemicals. For simultaneous saccharification and co-fermentation, a strain that can perform simultaneous saccharification and fermentation using $C_5$ and $C_6$ sugars as a carbon source may be used. In this case, the hexose and pentose sugars extracted from cellulose and/or hemicellulose may be mixed with each other, and used to produce biofuels or biochemicals in one batch. A process using simultaneous saccharification and a co-fermentation strain combines saccharification of a polysaccharide using a commercially available hydrolytic enzyme or enzyme-producing strain and fermentation using a fermenting strain.

Accordingly, in one example, saccharification may be performed by treatment with an enzyme, and fermentation may be performed using one or more fermenting microorganisms. Here, saccharification to produce a hydrolyzate can be performed by adding the pretreated biomass and a saccharification enzyme to a saccharification reaction vessel and saccharifying the biomass at an optimal temperature for the saccharification enzyme reaction to obtain the hydrolyzate. Fermentation may include adding microorganisms to a microorganism fermentation vessel, supplying the hydrolyzate, and culturing the microorganisms at an optimal temperature for fermentation.

These two steps may be simultaneously performed in a simultaneous saccharification and co-fermentation (SSCF) process. Compared to a conventional process in which saccharification and fermentation are separately performed, such an SSCF process can reduce the number of reactors and prevent product inhibition of saccharification by fermenting the produced sugar.

In the SSCF process, saccharification and fermentation can be performed simultaneously using one strain, and thus when such consolidated bioprocessing (CBP) is used, processing time and production costs can be significantly reduced due to the simultaneously-performed saccharification and fermentation.

3. Apparatus for Pretreating Biomass

Figure 5:
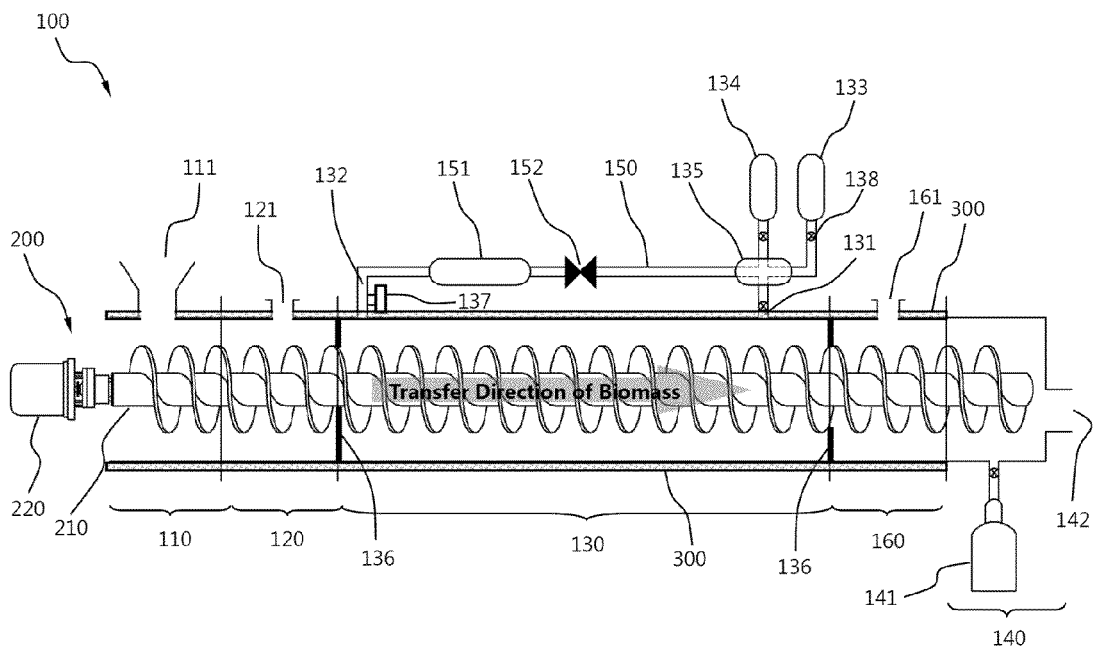
FIG. 5 is a schematic diagram of a pretreatment apparatus according to an exemplary embodiment.

In still another aspect, an apparatus for pretreating a biomass is provided, which can be used for the method of pretreating a biomass described above. A pretreatment apparatus 100 according to one exemplary embodiment is shown in FIG. 5, and with reference thereto, it will be described in detail.

The pretreatment apparatus 100 according to one exemplary embodiment includes a biomass supply part 110, a water supply part 120, a reaction part 130, and a separation part 140. The biomass supply part 110, the water supply part 120, the reaction part 130 and the separation part 140 may be independently or continuously formed. As the latter example, a continuous structure may be configured using a means capable of continuously transferring a biomass to these components. For example, a screw-type transfer apparatus 200 may be formed within and pass through these components. The transfer apparatus 200 may transfer a biomass by axial rotation of a screw 210. The axial rotation may be performed using a driving force provided by a motor 220 connected to the screw 210. Alternatively, the transfer apparatus 200 may continuously transfer the biomass using a conveyer belt.

The biomass supply part 110 is to provide the biomass, and includes a hopper 111 through which the biomass is input. If necessary, a fragmentation part (not shown) physically fragmenting the biomass and cutting or grinding the ingredients to approximately 0.1 to 5 cm may be included. The fragmentation part may include a cutter such as a knife cutter for fragmenting the biomass, which may be implemented through transformation of the screw 210 of the transfer apparatus 200 providing a driving force to transfer the biomass.

The water supply part 120 is to provide water to the biomass, and thus can be included if necessary. That is, in the pretreatment apparatus, to pretreat a dry biomass or a biomass containing insufficient water to support an internal heating reaction, the water supply part 120 should be included, but to pretreat a biomass containing sufficient water to support an internal heating, the water supply part 120 need not be included. The water supply part 120 may be connected to a water storage tank (not shown), which may be connected to an opening 121 of the water supply part 120.

The reaction part 130 is a place in which internal heating occurs. Herein, a water-reactive anhydride for the exothermic reaction may be continuously provided to the water-containing biomass, which received water from the water supply part 120 or contained sufficient water, and thereby the exothermic reaction occurs. If necessary, to prevent heat generated in the reaction part 130 from being transferred outside the apparatus, an outer surface of the reaction part 130 may be insulated. In order to maintain or adjust pressure in the reaction part 130 and prevent outflow of gas, partitions 136 may be formed at opposite ends of the reaction part 130, for example, between the water supply part 120 and the reaction part 130, and between the reaction part 130 and the separation part 140 or a washing part 160.

To supply or exhaust the water-reactive anhydride from the reaction part 130, an inlet part 131 and an outlet part 132 for the water-reactive anhydride may be formed at the opposite ends of the reaction part 130. For example, when the biomass is transferred through the reaction part 130 in one direction, the inlet part 131 for the water-reactive anhydride may be disposed at the end of the reaction part 130 opposite to the end at which the biomass is introduced, and the outlet part 132 may be disposed at the end of the reaction part 130 at which the biomass enters the reaction part 130. Disposing the inlet part 131 and outlet part 132 for the water-reactive anhydride such that the direction of flow of the water-reactive anhydride is the reverse of the direction of transfer of the biomass through reactor part increases the penetrability of the water-reactive anhydride into the biomass. Additionally, to obtain a sufficient temperature for pretreatment of the biomass, an adjustment of the internal heat produced is needed. The internal heating may be adjusted by adjusting the input flow rate or the input amount of the water-reactive anhydride at a static pressure, or by adjusting the pressure, the input amount or the input flow rate of the water-reactive anhydride at the same flow rate of biomass. In the latter case, the solubility of the water-reactive anhydride is increased under the increasing pressure, and thus heating through pressurization may be an easy way to adjust the input amount. Such an apparatus for pressurization may be, but is not particularly limited to, one that has a pressurized supply tank, or one that is pressurized by a separate pressure controller. A pressure regulator 137 may be installed at the inlet part 131 or the outlet part 132 to control and maintain the total pressure of the reactor.

A first supply tank 133 containing water-reactive anhydride may be connected to the inlet part 131. In addition, a second supply tank 134 containing water-reactive anhydride exhausted from the outlet part 132 or water-reactive anhydride recovered through dehydration and recompression is connected to the inlet part 131. Each supply tank 133 or 134 has a valve 138, which is opened or closed to control flow of the water-reactive anhydride into the reaction part 130. The water-reactive anhydride may be continuously supplied from the supply tank 133 or 134.

A bridge part 150 may be formed to connect the outlet part 132 to the inlet part 131, to transfer unreacted water-reactive anhydride exhausted from the outlet part 132 to the inlet part 131. By connecting the outlet part 132 and the inlet part 131 via the bridge part 150, the water-reactive anhydride that does not participate in the internal heating reaction may be recycled by expansion, dehydration, and recompression.

Further, the inlet part 131 may include a mixing part 135 for mixing the water-reactive anhydride supplied from the first and second supply tanks 133 and 134. The water-reactive anhydride recovered through the bridge part 150 is captured in the second supply tank 134, or directly flows into the mixing part 135, and then may be mixed with fresh water-reactive anhydride supplied from the first supply tank 133 and transferred to the inlet part 131.

For dehydration and recompression of the water-reactive anhydride exhausted from the outlet part 132, the bridge part 150 may include a dehydration column 151 and a compressor 152. For example, after the internal heating by the exothermic reaction is completed, a solution in which the water-reactive anhydride is dissolved is collected, dehydrated using a dehydrating agent in the dehydration column 151, and then compressed using the compressor 152 to be reduced into the anhydride. As such, the recovered water-reactive anhydride is captured in the second supply tank 134.

A washing part 160 for washing the biomass may be connected to the reaction part 130. The washing part 160 has an opening 161 through which water flows to the biomass like the water supply part 120, thereby removing an extracted component or solution in which the water-reactive anhydride is dissolved. To remove the solution, a pitch of the screw of the compressor may be decreased, or the screw may be disposed in a reverse direction, thereby increasing an internal pressure. For example, a black liquor in which lignin is dissolved may be selectively extracted through the storage part 141 disposed under the separation part 140 to be described in detail.

The separation part 140 separates components extracted from the biomass by the internal heating reaction, and has an exhaustion part 142 at its end, through which the biomass pretreated by internal heating is exhausted. In addition, at least one storage part 141 storing the components separated from the pretreated biomass may be connected to the separation part 140.

If necessary, additional reaction parts (not shown) may be included to pretreat, separate and extract non-separated components from the biomass. For example, after lignin is extracted from the lignocellulosic biomass in reaction part 130, hemicellulose and cellulose are residual components of the biomass. To separate and extract hemicellulose and cellulose from the biomass, an additional reaction part for treating the biomass with an acid solvent may be included. Such additional reaction parts may not be disposed at particularly limited locations, and may be connected to the reaction part 130, the washing part 160, or the separation part 140.

A process of pretreating the lignocellulosic biomass using the pretreatment apparatus 100 according to the exemplary embodiment is as follows.

First, the lignocellulosic biomass is input to the biomass supply part 110 through the hopper 111 to be ground and then transferred to the water supply part 120. A sufficient amount of water for inducing internal heating, for example, 0.5 to 3 times the weight of the biomass is added to the biomass in the water supply part 120 to produce a water-containing biomass. The water-containing biomass is then transferred to the reaction part 130. Anhydrous ammonia, for example, is supplied from the inlet part 131, which is disposed at the right end of reaction part 130. The anhydrous ammonia is stored in supply tank 133 under an increasing pressure, and then input to the inlet part 131 connected to the supply tank 133 while the flow rate of the anhydrous ammonia is adjusted according to the opening degree of the valve 138. The input anhydrous ammonia is dissolved in water, thereby emitting heat and resulting in conversion into aqueous ammonia (ammonium hydroxide). Due to the internal heating produced, the internal temperature of the closed reaction part 130 is increased within a short time, and lignin is eluted from the lignocellulose. Then, the biomass is transferred to the separation part 140 (or, if the washing part is present, transferred to the washing part 160). Furthermore, vapor generated due to the high temperature is mixed with the unreacted ammonia gas, and then exhausted to the outlet part 132. Internal pressure in reaction part 130 is uniformly maintained by the pressure regulator 137 installed at the outlet part 132. In addition, after the unreacted anhydrous ammonia containing a large amount of water is exhausted through outlet part 132, it passes through the dehydration column 151 of the bridge part 150, and is recompressed by the compressor 152 and stored in the second supply tank 134. After fresh anhydrous ammonia at a high concentration supplied from the first supply tank 133 and the anhydrous ammonia supplied from the second supply tank 134 are mixed with each other in the mixing part 135 to have a certain concentration, the mixture is transferred to the inlet part 131 through the valve 138 to be reused for a next cycle of the reaction.

When such an apparatus is used, a continuous process can be performed through the continuous input of the biomass and the continuous reaction with the anhydride.

Hereinafter, the disclosure will be described in further detail according to the following examples.

Example 1

After an equivalent amount of water (20 g) was added to 20 g of completely-dried fragmented rice straw to wet it, a reactor having an inner volume of 125 ml was filled with the wet rice straw. The reactor is closed, and anhydrous ammonia gas at a pressure of 50 psi was input to the reactor at room temperature (25° C.). The added ammonia gas dissolves in the water in the wet rice straw to rapidly induce internal heating within the reactor by the exothermic reaction. Afterwards, the input of ammonia gas was stopped. During such a batch-type reaction, the internal heating reaction generated heat that raised the temperature within the reactor to a maximum of 65° C. within 1 minute. Pretreatment of the rice straw was performed with the reactor in the room temperature environment for 1 hour without any external supply of heat. The delignification rate determined is shown in Table 1.

To determine the effect of temperature on delignification, a reactor was filled with the reactants, and its temperature was increased to 40° C. using an external electric heater. Afterwards, the external heat supply was stopped, and ammonia gas was input in the same process described above to produce internal heating by the exothermic reaction. In this experiment, the maximum temperature within the reactor at an initial state of the reaction was 83° C. Pretreatment of the rice straw was performed within the reactor for 1 hour. The delignification rate determined is shown in Table 1.

To determine the effect of time on delignification, ammonia gas was input to a reactor filled with the wet rice straw, and the internal temperature of the reactor was increased to 65° C. and maintained at 65° C. for 16 hours. The delignification rate determined is shown in Table 1.

The rice straw used as a biomass sample initially contained 39.4% cellulose, 23.5% hemicellulose, and 16.0% lignin. The delignification rate (%) determined is shown in Table 1.

Delignification Rate (%)=[(initial amount of lignin−amount of lignin after pretreatment)/initial amount of lignin]×100.

TABLE 1

Delignification rate (%) according to the internal temperature of the reactor

| Reaction Condition | Delignification Rate (%) |
|---|---|
| 65° C. + 1 hr (Initial Temperature = 25° C.) | 45.7 |
| 83° C. + 1 hr (Initial Temperature = 40° C.) | 53.6 |
| 65° C. + 16 hr (Initial Temperature = 25° C.) | 61.4 |

Comparative Example 1

To compare the effects of pretreatment using ammonia gas to a conventional pretreatment using an ammonia solution (e.g., soaking in aqueous ammonia), pretreatment was performed at different time and temperature conditions using 15% aqueous ammonia having an amount corresponding to 20 times the weight of fragmented rice straw. For a flask-scaled experiment, 100 ml of 15% aqueous ammonia was added to 5 g of the fragmented rice straw. Reactions were then performed at different temperatures for a predetermined time in a closed flask using a shaking temperature-controlled incubator capable. The delignification rates (%) determined as a function of time and temperature are shown in Table 2.

TABLE 2

Delignification rates (%) determined as a function of time and temperature

| Reaction Time (hr) | Reaction Temperature | | |
|---|---|---|---|
| | 25° C. | 60° C. | 80° C. |
| 0 | 0.0 | 0.0 | 0.0 |
| 1 | 5.1 | 6.1 | 8.4 |
| 2 | 22.0 | 26.3 | 38.4 |
| 4 | 27.1 | 40.0 | 55.7 |
| 8 | 32.4 | 46.6 | 60.7 |
| 16 | 34.5 | 59.5 | 64.0 |

Referring to Tables 1 and 2, Example 1 in which the reaction was performed for 1 hour after initially raising the internal reactor temperature to 65° C. exhibited a similar effect to Comparative Example 1 in which 15% aqueous ammonia was treated at 60° C. for 8 hours. Moreover, Example 1 in which the reaction was performed for 1 hour after initially raising the internal reactor temperature to at 83° C. exhibited a similar effect to Comparative Example 1 in which 15% aqueous ammonia was treated at 80° C. for 4 hours. In Example 1 in which an ammonia gas was used and the reaction was performed 1 hour after initially raising the internal reactor temperature to 65° C., there was no heat supply from outside, and although 1/20 of the water of Comparative Example 1 was input, Example 1 exhibited a significantly higher delignification effect than Comparative Example 1.

Example 2

A volume of 90, 180, or 300 ml of water is added to 30 g of biomass in a reactor, and a water-reactive anhydride gas is provided to each reactor at different pressures to generate internal heat. Then, the initial temperature in the reactor is measured. Temperature changes according to biomass (solid): water (liquid) (S:L) ratios and the pressure of ammonia gas in the reactors are shown in Table 3.

TABLE 3

Temperature changes according to biomass (solid):water (liquid) (S:L) ratios and the pressure of ammonia gas in the reactors

| | S:L = 1:3 | S:L = 1:6 | S:L = 1:10 |
|---|---|---|---|
| 15 psi | 50 | 62 | 63 |
| 25 psi | 63 | 65 | 66 |
| 50 psi | 76 | 80 | 82 |
| 70 psi | — | 89 | — |
| 100 psi | — | 99 | — |
| 120 psi | — | 115 | — |

Referring to Table 3, the temperature in the reactor is directly proportional to the amount of water and the pressure of ammonia gas. When a pressure of 50 psi or more is provided, a temperature sufficient for pretreatment can be obtained. Reaction time for pretreatment of the biomass can be reduced under the high-temperature condition.

Example 3

The fragmented rice straw pretreated for 1 hour after initially raising the internal reactor temperature to 65° C. by contacting anhydrous ammonia according to Example 1 was enzymatically saccharified using 50 mM citrate buffer at 50° C. according to a standard saccharification procedure of the National Renewable Energy Laboratory (NREL), United States Department of Energy, Technical Report NREL/TP-510-42629, March 2008. After the enzymatic saccharification, fermentation was performed using a pentose/hexose simultaneous fermentation strain. The yield of ethanol was 26.4 g based on 100 g of the fragmented rice straw.

Comparative Example 2

Fragmented rice straw pretreated at 60° C. for 8 hours by adding aqueous ammonia according to Comparative Example 1 was subjected to enzymatic saccharification. Pentose/hexose simultaneous fermentation was performed as in Example 3. The yield of ethanol was 25.5 g based on 100 g of the fragmented rice straw.

It can be seen that the yields of ethanol in Example 3 and Comparative Example 2 were quite similar to each other.

Example 4

To compare ethanol fermentation yields, rice straw pretreated with ammonia gas is compared with rice straw subjected to the conventional pretreatment methods of soaking in aqueous ammonia (SAA) or ammonia fiber expansion (AFEX). First, 100 g of rice straw was pretreated by each method. For the pretreatment with ammonia gas, 99.9% ammonia gas was supplied to wet rice straw at 50 psi for 1 hour without providing external heat as described in Example 1 above. For the SAA pretreatment (described in Comparative Example 1 above), 15% aqueous ammonia was supplied to the rice straw, and a reaction was performed at 60° C. and 250 rpm for 20 hours. For the AFEX pretreatment, 15% aqueous ammonia was supplied to the rice straw, and reaction was performed at 95° C. for 20 mins. Afterwards, each of the three pretreated samples was fermented using *E. Coli* cultured under identical conditions. Fermentation results are shown in Table 4. The pretreatment method disclosed herein, with ammonia gas, can produce a yield of 23.9% ethanol/ batch, which is less than that produced by SAA pretreatment, but higher than that produced by AFEX pretreatment.

TABLE 4

Fermentation results according to pretreatment methods

| | Rice straw (g) | Pretreated rice straw (g) | EtOH (g)/batch |
|---|---|---|---|
| Ammonia gas | 100 | 79.6 | 23.9 |
| SAA | 100 | 70.2 | 25.7 |
| AEEX | 100 | 82.3 | 22.7 |

According to a method of pretreating a biomass, internal heat is generated by a chemical reaction of a water-reactive anhydride with water in the biomass and the biomass is pretreated by the internal heating reaction. The biomass can be effectively pretreated, thereby greatly saving energy. In addition, the water-reactive anhydride can penetrate well into the biomass and have a sufficient exothermic reaction within a short time so that pretreatment time can be drastically reduced, and uniform pretreatment can be achieved in a very short time. Further, since the anhydride can induce a sufficient internal heating reaction with a small amount of water, a large amount of industrial water is not needed. As a result, production costs for supply of industrial water, heating and cooling of the industrial water, and treatment of waste water can be reduced. Thus, the scale of equipment and operating costs can be reduced, resulting in a decrease in production costs.

A method of producing bio fuels or biochemicals using such a pretreatment method has a high yield and low operating costs, which is effective in industrial implementation.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof. The modifier "about" used in connection with a quantity is inclusive of the stated value and has the meaning dictated by the context (e.g., includes the degree of error associated with measurement of the particular quantity).

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

What is claimed is:

1. An apparatus for pretreating a biomass, comprising:
   a reaction part for pretreating a biomass, the reaction part including
   an inlet part which is formed at a first end of the reaction part and through which a gaseous water-reactive anhydride can be input, wherein the inlet part is connected to a first supply tank containing fresh gaseous water-reactive anhydride, and
   an outlet part which is formed at a second end of the reaction part opposite the first end and through which the gaseous water-reactive anhydride can be output;
   a biomass supply part for supplying a biomass to the second end of the reaction part;
   a water supply part formed between the biomass supply part and the reaction part, and connected to the second end of the reaction part to supply water to the biomass;
   a washing part connected to the first end of the reaction part to wash the biomass, and
   a separation part connected to the washing part for separating components extracted from the biomass,
   wherein the inlet, outlet, and biomass supply parts are configured such that the direction of flow of the gaseous water-reactive anhydride through the reaction part is the reverse of the direction of transfer of the biomass through the reaction part.

2. The apparatus according to claim 1, wherein the biomass supply part, the reaction part and the separation part are continuously formed, and a screw transfer apparatus is formed inside to transfer the biomass continuously.

3. The apparatus according to claim 1, wherein an outer surface of the reaction part is insulated.

4. The apparatus according to claim 1, further comprising a fragmentation part formed between the biomass supply part and the reaction part to fragment the biomass.

5. The apparatus according to claim 1, further comprising a bridge part formed between the outlet part and the inlet part, to transfer fluid from the outlet part to the inlet part.

6. The apparatus according to claim 5, wherein the bridge part includes a dehydration column and/or a compressor.

7. The apparatus according to claim 1, further comprising a second supply tank in fluid connection with a dehydration column and/or a compressor.

8. The apparatus according to claim 7, further comprising a mixing part in fluid connection with the first supply tank, the second supply tank, and the inlet part.

9. The apparatus according to claim 5, wherein the outlet part includes an exhaustion part, which is separated from the bridge part, to exhaust a vapor generated by internal heating.

10. The apparatus of claim 3, wherein the apparatus does not comprise a heat source outside the reaction part.

11. An apparatus for pretreating a biomass, comprising:
a reaction part for pretreating a biomass, the reaction part including
an inlet part which is formed at a first end of the reaction part and through which a gaseous water-reactive anhydride can be input, wherein the inlet part is connected to a first supply tank containing fresh gaseous water-reactive anhydride, and
an outlet part which is formed at a second end of the reaction part opposite the first end and through which the gaseous water-reactive anhydride can be output;
a biomass supply part for supplying a biomass to the second end of the reaction part;
a washing part connected to the first end of the reaction part to wash the biomass, and
a separation part connected to the washing part for separating components extracted from the biomass;
wherein the reaction part is insulated, and the apparatus does not comprise a heat source outside the reaction part, and wherein the inlet, outlet, and biomass supply parts are configured such that the direction of flow of the gaseous water-reactive anhydride through the reaction part is the reverse of the direction of transfer of the biomass through the reaction part.

12. An apparatus for pretreating a biomass, comprising:
a reaction part for pretreating a biomass, the reaction part including
an inlet part which is formed at a first end of the reaction part and through which a gaseous water-reactive anhydride can be input, wherein the inlet part is directly connected or coupled to a first supply tank, and
an outlet part which is formed at a second end of the reaction part opposite the first end and through which the gaseous water-reactive anhydride can be output;
a biomass supply part for supplying a biomass to the second end of the reaction part;
a water supply part formed between the biomass supply part and the reaction part, and connected to the second end of the reaction part to supply water to the biomass;
a washing part connected to the first end of the reaction part to wash the biomass, and
a separation part connected to the washing part for separating components extracted from the biomass,
wherein the inlet, outlet, and biomass supply parts are configured such that the direction of flow of the gaseous water-reactive anhydride through the reaction part is the reverse of the direction of transfer of the biomass through the reaction part.

* * * * *